United States Patent [19]

Perrett

[11] 4,262,799
[45] Apr. 21, 1981

[54] SUPPORT POST BODY

[75] Inventor: Thomas R. Perrett, Bala Cynwyd, Pa.

[73] Assignee: Synthes AG, Chur, Switzerland

[21] Appl. No.: 64,534

[22] Filed: Aug. 7, 1979

[51] Int. Cl.³ .................. B65D 82/00; A61L 2/00; A61L 9/00
[52] U.S. Cl. .................. 206/363; 206/493; 422/300; 211/60 T; 211/59.1
[58] Field of Search .............. 206/363, 349, 493, 303, 206/370; 248/309, 309 A; 422/300, 297; 211/60 I, 60 R, 13, 59.1

[56] References Cited
U.S. PATENT DOCUMENTS

| | | | |
|---|---|---|---|
| 1,966,247 | 7/1934 | Janssen | 248/309 A |
| 2,963,147 | 12/1960 | Stagner | 206/493 |
| 3,255,987 | 6/1966 | Gatch | 211/59.1 |
| 3,291,429 | 12/1966 | Neanhouse | 248/309 |
| 3,540,576 | 11/1970 | Pierce | 206/303 |
| 3,674,138 | 7/1972 | Gilmour | 206/493 |
| 4,043,754 | 8/1977 | Sklar | 211/60 T |

Primary Examiner—William T. Dixson, Jr.

Attorney, Agent, or Firm—Davis, Hoxie, Faithfull & Hapgood

[57] ABSTRACT

An integral support post body adapted for mounting in an aperture in a bottom plate of a medical device sterilization case, said body comprising a disk-shaped base whose maximum transverse dimension is greater than the maximum transverse dimension of said aperture, a reduced diameter; cylindrical neck; and a generally frusto-conical tip which comprises an extended frusto-conical side wall extending both upwardly in a direction away from said neck and inwardly and a convex top wall of a transverse peripheral configuration which conforms to and merges with the upper extremity of said side wall, the maximum transverse dimension of said side wall at its lower extremity being greater than the maximum transverse dimension of said aperture and the maximum transverse dimension of said side wall at its upper extremity being less than or equal to the corresponding transverse dimension of said aperture, and the axial length of said body being sufficient that the clearance between the undersurface of the top wall of the case and the upper extremity of the top surface is less than the vertical dimension of a medical device to be supported by said body.

3 Claims, 3 Drawing Figures

SUPPORT POST BODY

BACKGROUND OF THE INVENTION

The present invention relates to a support for holding medical devices in a case against lateral shifting.

SUMMARY OF THE INVENTION

It is an object of the present invention to provide a support for use in conjunction with a case for supporting a medical instrument against undesired lateral shifting movement of the instrument.

This and other objects are provided in accordance with the present invention by an integral support post body adapted for mounting in an aperture in a bottom plate of a medical device sterilization case. The said body comprises a disk-shaped base whose maximum transverse dimension is greater than the maximum transverse dimension of said aperture; a reduced diameter, cylindrical neck; and a generally frusto-conical tip comprising an extended frusto-conical side wall which extends upwardly in a direction away from said neck and inwardly and a convex top wall of a transverse peripheral configuration which conforms to and merges with the upper extremity of said side wall, the maximum transverse dimension of said side wall at its lower extremity being greater than the maximum transverse dimension of said aperture and the maximum transverse dimension of said side wall at its upper extremity being less than or equal to the corresponding transverse dimension of said aperture, and the axial length of said body being sufficient that the clearance between the undersurface of the top wall of the case and the upper extremity of the top surface is less than the vertical dimension of a medical device to be supported by said body.

BRIEF DESCRIPTION OF THE DRAWINGS

The preferred embodiment of the present invention will be described in detail with reference to the accompanying drawing in which.

DESCRIPTION OF THE PREFERRED EMBODIMENTS

The support post of the present invention comprises an integral support post body 1 which is composed of a sterilizable polymeric material, such as the synthetic resinous plastic material marketed by E. I. duPont de Nemours and Company under the designation DELRIN.

Figure 1:
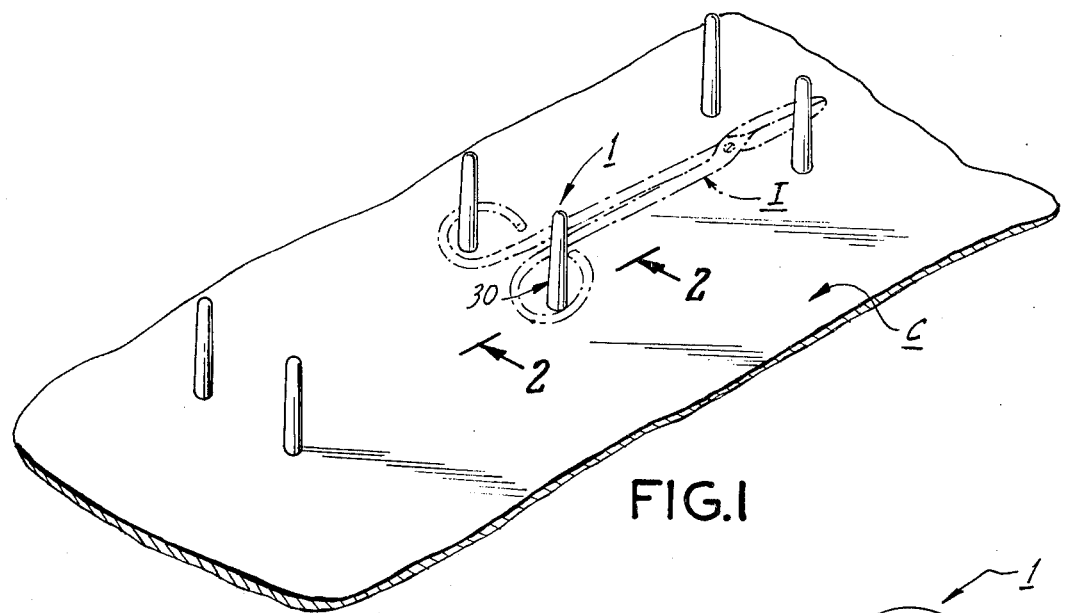
FIG. 1 is a perspective view showing a fragment of the bottom plate of a medical device sterilization case C with a plurality of support post bodies 1 of the present invention mounted on it and also a phantom showing (by a dot-dash line) of a medical device I positioned by several of the bodies 1.

The support post 1 is adapted to be mounted through a circular aperture O in the bottom wall or plate, B of a medical device sterilization case C (FIG. 1) so as to extend perpendicularly of the bottom wall B and prevent undue lateral shifting of a medical instrument I or other medical device, such as an orthopedic implant.

Figure 3:
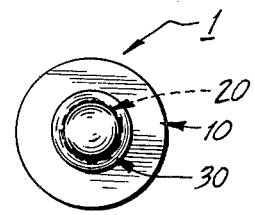
FIG. 3 is a top plan view of a support post body 1 of the present invention.
Figure 2:
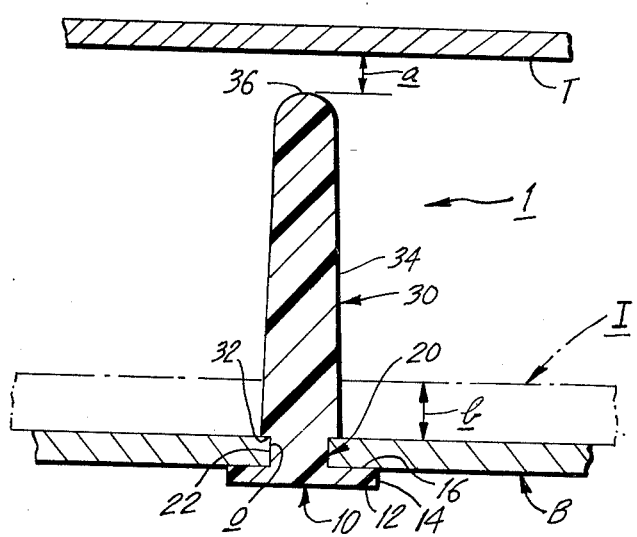
FIG. 2 is a side elevation view, in section taken along the line 2—2 in FIG. 1, of a support post body 1 of the present invention mounted on the bottom plate B showing the body's relationship to a top wall T and a medical device I (shown by a dot-dash line)

The body 1 (FIGS. 2 and 3) includes a base 10 and a tip 30 interconnected by a reduced diameter, cylindrical neck 20. The disk-shaped base 10, in turn, comprises a circular bottom wall 12 connected to an upstanding vertical cylindrical side wall 14 surmounted by a horizontal annular top wall 16. The maximum transverse dimension, or diameter, of the base 10 is greater than the corresponding maximum transverse dimension, or diameter, of the aperture O so that the top wall 16 abuts the undersurface of the plate B and the base 10 acts as a stop against upward movement of the body 1.

The vertically oriented neck 20 is provided with a cylindrical side wall 22 which fits into the aperture O and has a diameter approximately equal to the diameter of aperture O and a height approximately equal to the thickness of the bottom plate B so as to prevent rocking the body 1.

The generally frusto-conical tip 30 is connected to the neck 20 by a horizontal annular undersurface 32 and has an extended frusto-conical side wall 34 which tapers inwardly and upwardly toward a convex, preferably hemispheric, top surface 36 so that the maximum transverse dimension, or diameter, of the side wall 34 at its lower extremity (the intersection with the undersurface 32) is greater than the maximum transverse dimension, or diameter, of the aperture O while being approximately equal to the corresponding aperture dimension at its upper extremity where it merges into top surface 36. Consequently, while the post body 1 can be pressed through the aperture O, tip first, the undersurface 32 abuts against the top surface of plate B and prevents retrograde movement of the body 1 when the body 1 is in its installed position. The top surface 36 is provided with a peripheral transverse configuration which conforms to and merges with the upper extremity of the side wall 34. This merger and the rounded top surface facilitate insertion of the body 1 in the aperture O.

The post body 1 is installed in the bottom plate B by moving the body 1 axially partially through aperture O by passing the top surface 36 and then the side wall 34 of tip 30 into and through the aperture O until the side wall 34 engages aperture O, at which point the body 1 is pressed home, forcing the remainder of the side wall 34 to pass through the aperture O until the reduced diameter side wall 22 of neck 20 rests in the aperture O and the top wall 16 of base 10 abuts the lower surface of plate B.

The axial length of post body 1 should be sufficient that the clearance a between undersurface of the top plate T of the instrument case C (FIG. 2) and the uppermost extremity of top surface 36 is less than the vertical dimension b of the instrument I. While the instrument I, or other device, can shift laterally slightly, and vertically to the extent of the interior height of the case, it is not able to move freely across the length and width of the interior of case C. By mounting a plurality of support post bodies (FIG. 1) through the bottom plate B of the case C, it is possible to further control each instrument. The plate B may either be the bottom wall of the plate/wall case C or a separate, horizontally disposed plate member placed in the bottom of the case C and the terms "bottom plate" or "bottom wall" should be so construed.

It should be understood that, while the support post of the present invention has been described for use in association with instruments, it can also be used in association with other medical devices such as orthopedic implants and the like.

While specific embodiments of the present invention have been shown and described in the specification and drawings to illustrate and explain the present invention, it should be understood that the present invention is not limited to these specific embodiments, but contemplates other embodiments falling within the scope of the following claims.

I claim:

1. In a medical device sterilization case which is adapted to support a medical device during sterilization and which includes an apertured bottom plate, a top wall disposed in spaced relationship above said bottom plate and at least one integral support post body disposed in mounted relation with an aperture of said bottom plate, the improvement comprising
   1. said aperture being circular,
   2. said support post body comprising
       a. a disk-shaped base whose maximum transverse dimension is greater than the maximum transverse dimension of said aperture;
       b. a reduced diameter, cylindrical neck comprising a cylindrical side wall having a diameter approximately equal to the diameter of said aperture and a height approximately equal to the thickness of said bottom plate; and
       c. a generally frusto-conical tip comprising
           i. an extended frusto-conical side wall which extends upwardly in a direction away from said neck and inwardly and
           ii. a convex top wall provided with a transverse peripheral configuration which conforms to and merges with the upper extremity of said side wall,
           iii. the maximum transverse dimension of said side wall at its lower extremity being greater than the maximum transverse dimension of said aperture and
           iv. the maximum transverse dimension of said side wall at its upper extremity being less than or equal to the corresponding transverse dimension of said aperture, and
   3. the axial length of said body being sufficient that the clearance between the undersurface of the top wall of the case and the upper extremity of the top surface is less than the vertical dimension of a medical device to be supported by said body.

2. A support post body in accordance with claim 1, wherein said base comprises
   a circular bottom wall,
   a cylindrical side wall and,
   an annular top wall.

3. A support post body in accordance with claim 1, wherein said body is composed of a sterilizable synthetic polymeric material.

* * * * *